United States Patent [19]

Nakano et al.

[11] Patent Number: 5,106,868
[45] Date of Patent: Apr. 21, 1992

[54] EPOXYCYCLOHEXENONE AMIDES WITH ANTIBACTERIAL ACTIVITY

[75] Inventors: Hirofumi Nakano; Mitsunobu Hara; Yutaka Saito; Yoji Ikuina, all of Tokyo; Toshimitsu Takiguchi; Masami Okabe, both of Shizuoka, all of Japan

[73] Assignee: Kyowa Hakko Kogyo Kabushiki Kaisha, Japan

[21] Appl. No.: 696,610

[22] Filed: May 7, 1991

[30] Foreign Application Priority Data

May 10, 1990 [JP] Japan .................................. 2-120640
Nov. 22, 1990 [JP] Japan .................................. 2-320439

[51] Int. Cl.$^5$ .................... A61K 31/12; A61K 31/335; C07D 303/36
[52] U.S. Cl. .................................. 514/475; 435/123; 435/252.5; 549/546
[58] Field of Search ......................... 549/546; 514/475

[56] References Cited

U.S. PATENT DOCUMENTS 4,116,984  9/1978  Prinzbach et al. .................. 549/546
4,226,879  10/1980  Omura et al. ........................ 514/475
4,595,770  6/1986  Brodasky et al. .................... 549/546

OTHER PUBLICATIONS

*The Journal of Antibiotics* 876, A New Antibiotic, Asukamycin, Produced by Streptomyces (Sep., 1976).
*The Journal of Antibiotics* 950, U-56,407, A New Antibiotic Related to Asukamycin: Isolation and Characterization (Aug., 1983).
The Journal of Antibiotics 1631, MM 14201, A New Epoxyquinone Derivative with Antibacterial Activity Produced by a Species of Streptomyces (Dec., 1983).
The Journal of Antibiotics 1530, The Structure of Manumycin (Nov. 1987).
16 *International Journal of Systematic Bacteriology* 313-340, E. B. Shirling and D. Gottlieb, Methods for Characterization of Streptomyces Species (Jul. 1966).
110 Chemical Abstracts 4225, Ralph Grote, et al., Metabolic Products of Microorganisms 244 (Jan. 2, 1989).
110 Chemical Abstracts 4225, Ralph Grote, et al., Metabolic Products of Microorganisms 245 (Jan. 2, 1989).

*Primary Examiner*—J. E. Evans
*Attorney, Agent, or Firm*—Schweitzer, Cornman & Gross

[57] ABSTRACT

Compounds UCF1 and derivatives thereof exhibit antibacterial and anti-tumor activities and may be used for the preparation of anti-bacterial and anti-tumor agents.

Compounds UCF1 may be produced by fermentation of a microorganism of the genus Streptomyces capable of producing compounds UCF1, preferably Streptomyces sp. UOF1 (FERM BP-2844) and recovering the desired compounds from the cultured broth.

The compounds UCF1 have the formula

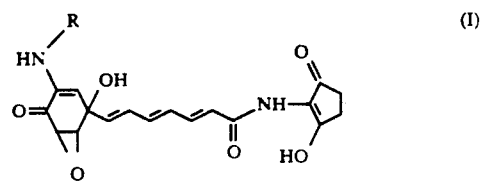

wherein R represents either

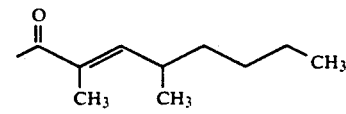

or

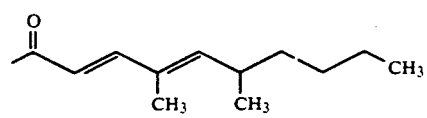

The compounds may be oxidized to obtain derivatives of formula

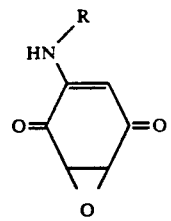

which exhibit similar pharmacological activities.

2 Claims, No Drawings

EPOXYCYCLOHEXENONE AMIDES WITH ANTIBACTERIAL ACTIVITY

The present invention relates to compounds hereinafter collectively designated UCF1, derivatives thereof and processes for their preparation. The compounds and derivatives of the present invention exhibit anti-bacterial and anti-tumour activities and may be used for the preparation of anti-bacterial and anti-tumour agents.

The following known compounds have anti-bacterial and anti-tumour activities:

(1) Manumycin:

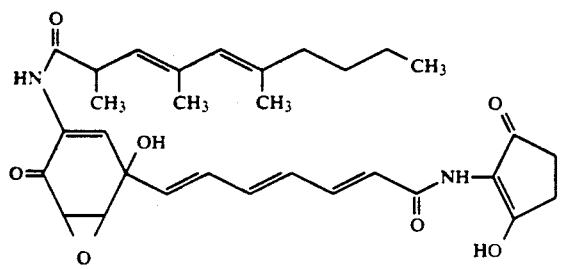

[disclosed in J. Antibiotics. 40 (11) 1530 (1987)].

(2) Asukamycin and U-56407:

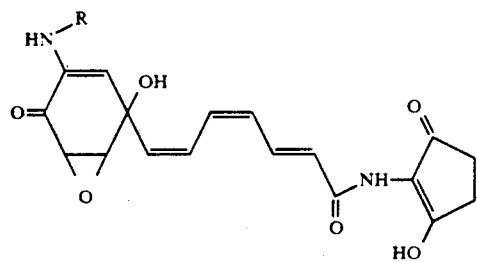

{wherein R is either

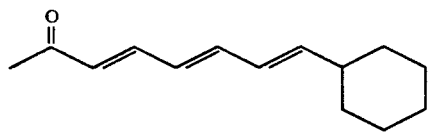

[Asukamycin disclosed in J. Antibiotics, 29 (9) 876 (1976)]
or

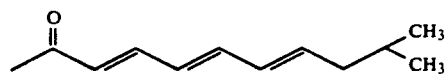

{U-56407, ibid. 36 (8) 950 (1983)]}.

(3) MT36531:

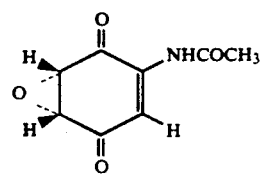

[disclosed in J. Antibiotics, 36 (12) 1631 (1983)]

The present invention is based upon the discovery that new compounds having high anti-bacterial and anti-tumour activities may be obtained by fermentation of a microorganism of the genus Streptomyces, which we have isolated from the soil at Numazu-shi, Shizuoka-ken, Japan.

Therefore the present invention is directed to provide new compounds and derivatives having high anti-bacterial and anti-tumour activities and processes for their preparation.

According to one aspect of the present invention, there are provided compounds represented by the following formula (I):

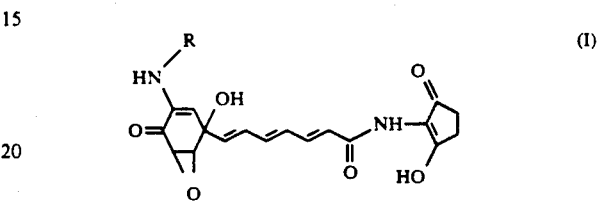

[wherein R represents either

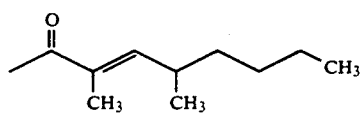

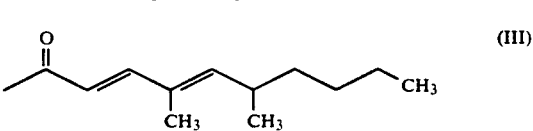

]. Compounds of the formula (I) wherein R represent (II) and (III) are respectively designated UCF1-A and UCF1-B hereinafter.

It has been found that the compounds of the formula (I) are new compounds and may be used for the preparation of anti-bacterial and anti-tumour agents by virtue of their physiological activities.

Another aspect of the present invention provides derivatives of UCF1, represented by the following formula (IV):

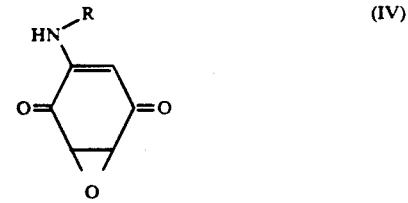

[wherein R represents either

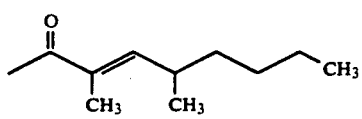

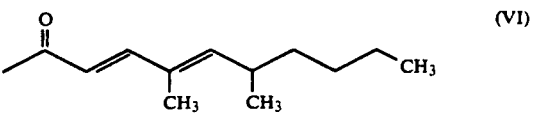

]. Compounds of the formula (IV) wherein R represent (V) and (VI) are designated respectively UCF1-AX and UCF1-BX hereinafter.

The above-mentioned derivatives may be used for the preparation of anti-bacterial and anti-tumour agents by virtue of their anti-bacterial and anti-tumour activities.

The compounds UCF1 of the present invention may be produced by fermentation of a microorganism of the genus Streptomyces capable of producing UCF1 in a medium to accumulate the desired compounds in the cultured broth and the cells, and recovering the desired compounds therefrom.

UCF1-AX and UCF1-BX, the derivatives of UCF1 of the present invention may respectively be obtained by subjecting compound UCF1-A and UCF1-B to oxidation in an organic solvent in a conventional manner.

The physico-chemical characteristics of UCF1-A, UCF1-B, UCF1-AX and UCF1-BX are as follows:

UCF1-A

1) Appearance: yellow powder
2) Melting point: >96° C. (decomposed)
3) Molecular formula: $C_{28}H_{34}N_2O_7$
4) Secondary ion mass spectrum (m/z): 511 $(M+1)^+$
5) Elemental analysis: Calculated (½ $H_2O$): C: 64.73, H: 6.79, N: 5.39; Found C: 64.69, H: 6.74, N: 5.27.
6) Specific rotation: $[\alpha]_D^{24} = -159°$ (c=0.1 in chloroform)
7) UV absorption spectrum (in methanol): $\lambda_{max}\ nm\ (\epsilon)$ 265(29,600), 282(30,300), 313(31,100)
8) IR absorption spectrum (KBr tablet method): $cm^{-1}$ 3398, 1672, 1624, 1603, 1514, 1367, 1005
9) Colour reaction: Positive in the reactions with vanillin/sulfuric acid, Ehrlich's reagent, iodine and ferric chloride.
10) Solubility in various solvents: Soluble in chloroform, dimethylsulfoxide, ethyl acetate, methanol and acetone. Insoluble in n-hexane and water.
11) $^1$H-NMR spectrum (in $CDCl_3$): δ (ppm) 13.62 (1H, br), 7.95 (1H, s), 7.85 (1H, brs), 7.38 (1H, d), 7.32 (1H, dd), 6.54~6.64 (2H, m), 6.41 (1H, dd), 6.21 (1H, dd), 6.12 (1H, d), 5.85 (1H, d), 3.71 (1H, dd), 3.65 (1H, d), 2.57 (4H, brs), 2.43~2.53 (1H, m), 1.89 (3H, d), 1.16~1.48 (6H, m), 1.00 (3H, d), 0.88 (3H, t)
12) $^{13}$C-NMR spectrum (in chloroform): δ (ppm) 197.4 (s), 189.0 (s), 174.4 (s), 168.1 (s), 165.6 (s), 144.8 (d), 143.4 (d), 139.5 (d), 136.5 (d), 131.7 (d), 131.5 (d), 129.2 (s), 128.0 (s), 126.5 (d), 121.7 (d), 115.1 (s), 71.2 (s), 57.4 (d), 52.9 (d), 36.6 (t), 33.3 (d), 32.2 (t), 29.7 (t), 25.9 (t), 22.8 (t), 20.1 (q), 14.0 (q), 12.6 (q)

UCF1-B

1) Appearance: yellow powder
2) Melting point: >188° C. (decomposed)
3) Molecular formula: $C_{30}H_{36}N_2O_7$
4) Secondary ion mass spectrum (m/z): 537 $(M+1)^+$
5) Elemental analysis: Calculated (+½ $H_2O$): C: 66.04, H: 6.84, N: 5.13; Found C: 65.64, H: 6.84, N: 4.92.
7) Specific rotation: $[\alpha]_D^{24} = +101°$ (c=0.1 in chloroform)
8) UV absorption spectrum (in methanol): $\lambda_{max}\ nm(\epsilon)$ 279(54,500), 315(38,800)
9) IR absorption spectrum (KBr tablet method): $cm^{-1}$ 3354, 1664, 1630, 1616, 1597, 1522, 1363, 1014
10) Colour reaction: Positive in the reactions with vanillin/sulfuric acid, Ehrlich's reagent, iodine and ferric chloride.
11) Solubility in various solvents Soluble in chloroform, dimethylsulfoxide, ethyl acetate, methanol and acetone. Insoluble in n-hexane and water.
12) $^1$H-NMR spectrum (in dimethylsulfoxide-$d_6$): δ (ppm) 9.72 (1H, brs). 9.14 (1H, s), 7.19 (1H, dd), 7.13 (1H, d), 7.08 (1H, d), 6.72 (1H, dd), 6.54 (1H, dd), 6.51 (1H, d), 6.50 (1H, dd), 6.40 (1H, d), 6.26 (1H, brs), 5.98 (1H, d), 5.68 (1H, d), 3.69 (1H, dd), 3.66 (1H, d), 2.45~2.55 (1H, m), 2.40 (4H, s), 1.74 (3H, s) 1.12~1.38 (6H, m), 0.94 (3H, d), 0.83 (3H, t)
13) $^{13}$C-NMR spectrum (in dimethylsulfoxide-$d_6$): δ (ppm) 189.5 (s), 186.9 (s), 165.6 (s), 165.2 (s). 146.9 (d), 145.9 (d), 141.6 (d), 139.2 (d), 139.1 (d), 131.4 (d), 131.2 (s), 130.0 (d), 128.8 (d). 128.1 (s), 123.0 (d), 119.5 (d), 114.3 (s), 70.7 (s), 56.5 (d), 52.4 (d), 36.4 (t), 32.5 (d), 29.2 (t), 29.0 (t), 22.2 (t), 20.4 (q), 13.9 (q), 12.4 (q)

UCF1-AX

1) Appearance: yellow oil
2) Molecular formula: $C_{16}H_{21}NO_4$
3) Electron ionization mass spectrum (m/z): 291 $(M)^+$
4) High resolution mass spectrum (m/z): Calculated as $C_{16}H_{21}NO_4$ 291.1470; Found 291.1436.
5) Specific rotation: $[\alpha]_D^{24} = +16°$ (c=0.2 in chloroform)
6) UV absorption spectrum in methanol: $\lambda_{max}\ nm(\epsilon)$ 326(3,900),
7) IR absorption spectrum (KBr tablet method): $cm^{-1}$ 3386, 1676, 1608, 1504,
8) Colour reaction: Positive in the reactions with vanillin-sulfuric acid, Ehrlich's reagent, iodine and ferric chloride.
9) Solubility in various solvents: Soluble in chloroform, methanol and diethyl ether. Insoluble in water.
10) $^1$H-NMR spectrum (in $CDCl_3$): δ (ppm) 8.25 (1H, brs), 7.58 (1H, d), 6.27 (1H, dd), 3.93 (1H, d), 3.84 (1H, dd), 2.46~2.57 (1H, m), 1.92 (3H, d), 1.18~1.48 (6H, m), 1.03 (3H, d), 0.89 (3H, t)
11) $^{13}$C-NMR spectrum (in $CDCl_3$): δ (ppm) 191.1 (s), 188.5 (s), 167.7 (s). 146.3 (d). 139.0 (s), 129.3 (s), 115.1 (d), 53.9 (d), 52.6 (d), 36.5 (t), 33.5 (d), 29.7 (t), 22.8 (t), 20.0 (q), 14.0 (q), 12.6 (q)

UCF1-BX

1) Appearance yellow oil
2) Molecular formula: $C_{18}H_{23}NO_4$
3) Electron ionization mass spectrum (m/z): 317 $(M)^+$
4) High resolution mass spectrum (m/z): Calculated as $C_{18}H_{23}NO_4$ 317.1627; Found: 317.1614.
5) Specific rotation: $[\alpha]_D^{24} = -14°$ (c=0.2 in chloroform)
6) UV absorption spectrum (in methanol): $\lambda_{max}\ nm\ (\epsilon)$ 270(16,500), 327(14,300)
7) IR absorption spectrum (KBr tablet method): $cm^{-1}$ 3313, 1695, 1670, 1604, 1506
8) Colour reaction: Positive in the reactions with vanillin-sulfuric acid, Ehrlich's reagent, iodine and ferric chloride.
9) Solubility in various solvents: Soluble in chloroform, methanol and diethyl ether. Insoluble in water.
10) $^1$H-NMR spectrum (in $CDCl_3$): δ (ppm) 7.86 (1H, brs), 7.63 (1H, d), 7.36 (1H, d), 5.85 (1H, d), 5.78 (1H, d), 3.92 (1H, d), 3.83 (1H, dd), 2.50~2.60 (1H, m), 1.80 (3H, d), 1.14~1.43 (6H, m), 1.00 (3H, d), 0.87 (3H, t)
11) $^{13}$C-NMR spectrum (in $CDCl_3$): δ (ppm) 191.0 (s), 188.3 (s), 165.2 (s), 151.1 (d), 150.5 (d), 139.1 (s), 131.0

(s), 116.5 (d), 115.2 (d), 53.9 (d), 52.5 (d), 36.9 (t), 33.5 (d), 29.7 (t), 22.8 (t), 20.4 (q), 14.0 (q), 12.5 (q)

The physiological characteristics of the present compounds and derivatives are as follows.

(A) Anti-bacterial activity:

Minimum inhibitory concentration (μg/ml) was measured by the agar dilution method using a medium (pH=7.0) which was prepared by dissolving Bactotryptone medium (3 g; commercial product of Difco, U.S.A.), meat extract (3 g), yeast extract (1 g), glucose (1 g) and agar (16 g) in water (1 l). The results are shown in the following Table 1.

TABLE 1

| Organism | A | B | AX | BX | Ma |
|---|---|---|---|---|---|
| 1 | 2.6 | 2.6 | 10 | 8.3 | 1.3 |
| 2 | 10 | 10 | 10 | 0.65 | 2.6 |
| 3 | 10 | 1.3 | 1.3 | 0.16 | 0.3 |
| 4 | >100 | >100 | 21 | >100 | >100 |
| 5 | >100 | >100 | 21 | >100 | >100 |
| 6 | >100 | >100 | 83 | 83 | >100 |
| 7 | >100 | >100 | 21 | >100 | >100 |
| 8 | >100 | >100 | 10 | >100 | >100 |
| 9 | >100 | >100 | 10 | 42 | 21 |

Notes:
A UCF1-A; B UCF1-B; AX UCF1-AX; BX UCF1-BX; Ma Manumycin (control);
1 Staphylococcus aureus ATCC 6538P;
2 Enterococcus faecium ATCC 10541;
3 Bacillus subtilis No. 10707;
4 Klebsiella pneumonia ATCC 10031;
5 Escherichia coli ATCC 26;
6 Pseudomonas aeruginosa Bin H No. 1;
7 Salmonella typhi ATCC 9992;
8 Shigella sonnei ATCC 9290;
9 Candida albicans ATCC 10231

(B) Anti-tumour activity:

MCF7 cells (ATCC HTB22) was add to RPMI-1640 medium (commercial product of Gibco, U.S.A.) containing 10 % fetal calf serum, insulin (10 μg/ml) and estradiol ($10^{-8}$M) (hereinafter referred to as medium A) to prepare a cell suspension containing $4.5 \times 10^4$ cell/ml.

On each occasion, 0.1 ml of the suspension was poured into each well of a 96 well microtitre plate and incubated at a temperature of 37° C. for 20 hours in a carbon dioxide incubator. Then a test compound (each 0.05 ml) was added to each well, followed by incubation similarly for 72 hours. After removal of the supernatant, another medium (0.1 ml) containing medium A and 0.02% neutral red was added to the material for incubating similarly for one hour to dye the cells. The supernatant was removed, and the residue was washed once with physiological Saline. Then the dyestuff was removed by using an aqueous solution of ethanol (30%) containing 0.001N hydrochloric acid.

The absorptivity at 550 nm of the material was measured by the use of a microplate reader. The absorptivity of the treated cells was compared with the absorptivity of untreated cells to measure the $IC_{50}$ value viz. the concentration of the test compound required to inhibit the growth of the cells by 50%. The results are shown in the following table.

TABLE 2

| Compound | $IC_{50}$ (μg/ml) |
|---|---|
| UCF1-A | 12.5 |
| UCF1-B | 7.3 |
| UCF1-AX | 18.9 |
| UCF1-BX | 7.5 |
| Manumycin (control) | 8.3 |

Preparation of compounds UCF1

Compounds UCF1 of the present invention may be obtained by culturing a microorganism belonging to the genus Streptomyces capable of producing UCF1 in a medium to accumulate UCF1 in the cultured broth, and recovering the desired compounds therefrom.

For the purpose of the present invention, it is possible to use any and all strains of the genus Streptomyces such as, for example, naturally-occurring or artificially-induced mutant strains thereof so far as they are capable of producing the desired compounds UCF1 by fermentation.

In one preferred embodiment, a strain designated by us as Streptomyces sp. UOF1 is used.

The following mycological characteristics of strain UOF1 were investigated using the E.B. Sherling method, recommended by the ISP (International Streptomyces Project) for identifying the characteristics of the strains of Streptomyces as well as by using the D. Gottlieb method disclosed in Int. J. Syst. Bacteriol., 16, 313-340 (1966). Diaminopimellic acid isomers were obtained by hydrolysis of the cell wall and identified with reference to the method of B. Becker et al [Appl. Microbiol., 12, 421-423 (1964)]. The morphology of the cell surfaces was observed by using an optical microscope, and the surfaces of the spore was observed by a scanning electron microscope. The colour names were designated with reference to Color Harmony Manual, the 4th Edition, published by the Container Corpn. of America (1958).

(1) Morphology:
Aerial mycelium: branched.
Vegetative hypha: branched. No fragment.
Spore: growing as a curly or loopy long chain having at least 10 to 30 arthrospores on the aerial mycelium.
Surface of the spore: smooth.
Shape and size of the spore: oval, 0.5×0.7 μm.
Sclerotium and sporangium: not found.

(2) Colour tone:
Aerial mycelium: gray.
Vegetative hypha: light yellow.
Melanoid pigment: not found.

(3) Chemical composition of the cell wall:
Stereotype of diaminopimellic acid: LL type.

(4) Assimilability of carbon sources:
Assimilable: glucose, xylose, mannitol, arabinose, rhamnose, inositol, lactose, galactose.
Not assimilable: raffinose, salicin, sucrose.
Liquefaction of gelatin: negative.
Hydrolysis of starch: positive.
Coagulation of skimmed milk: negative.
Decomposition of cellulose: positive.
Growth temperature*: 16° to 37° C. (optimal 28° to 32° C.)

(* Measured after culturing for 2 days).

The actions of this strain for gelatin, skimmed milk and cellulose were observed after culturing at a temperature of 28° C. for one month. Other characteristics were observed after culturing at a temperature of 28° C. for two weeks.

(5) Growth on various agar media:
The following table indicates the results which were obtained by culturing strain UOF1 on various media at a temperature of 28° C. for two weeks.

TABLE 3

| Agar medium | Results |
|---|---|
| Sucrose-nitrate | G: Poor |
| | AM: Moderate. White(a) |
| | SM: Colourless |
| | P: Not found |
| Glucose-asparagine | G: Good |
| | AM: Abundant. Natural (3dc)~white(a) |
| | SM: Pearl pink(3ca)~light tan(3gc) |
| | P: Found. Light yellow. |
| Glycerol-asparagine | G: Good. |
| | AM: Abundant. Grieg(1fe)~pearl(3ba) |
| | SM: Cork tan(4ie)~light apricot(4ea) |
| | P: Found. Light yellow. |
| Starch | G: Good. |
| | AM: Abundant. Grieg(1fe)~pearl(3ba) |
| | SM: Dusty coral(6gc)~cedar(6le) |
| | P: Not found |
| Tyrosine | G: Good. |
| | AM: Abundant. Grieg(1fe) |
| | SM: Dusty coral(6gc)~copper tan(5ie) |
| | P: Found. Light yellow. |
| Nutrient | G: Good. |
| | AM: Moderate. Grieg(1fe) |
| | SM: Copper tan(5ie)~dark redwood (6lg) |
| | P: Found. Light yellow. |
| Yeast-malt-extract | G: Good. |
| | AM: Moderate. Fresh pink(6ca) |
| | SM: Light persimmon(5ic) |
| | P: Found. Light yellow. |
| Oatmeal | G: Good. |
| | AM: Abundant. Natural(3dc) |
| | SM: Cocoa brown(5lg) |
| | P: Found. Light yellow. |
| Peptone-yeast extract-iron | G: Good. |
| | AM: Not found. |
| | SM: Peach tan(5gc) |
| | P: Not found |

Notes -
G Growth degree.
AM Formation and colour tone of aerial mycelia.
SM Colour tone of vegetative hyphae.
P Colour tone of soluble pigment.

(6) Identification of strain UOF1:

With respect to the existence of LL-type diaminopimellic acid, strain UOF1 had preliminarily been classified into the Cell wall I-type according to the classification of Actinomycetes by M. P. Lechevalier and H. A. Lechevalier [Int. J. Syst. Bacteriol., 20, 435-443 (1970)]. As a result of further studies of the morphological characteristics of UFO1, this strain has been classified into Streptomyces.

With regard to the identification of the species of strain UOF1, various species recognized by learned societies [Int. J. Syst. Bacteriol. 30, 225-420 (1980) authored by V. D. B. Skerman et al.] were studied to discover a candidate on the basis of various characteristics such as the aerial mycelium coloured in gray to white, the spore chain in the form of a curl or loop, the smooth surface of spore, the productivities of melanoid pigment and soluble pigment as well as the assimilability of carbon sources, with reference to the reports by ISP [ibid., 18, 69-189 (1968); ibid., 18, 279-392 (1968); ibid., 19, 391-512 (1969); and ibid., 22, 265-394 (1972)] and to Bergy's Manual of Determinative Bacteriology, [8th Edition, edited by R. E. Buchanan and N. E. Gibbons]. As a result, it was noted that *Streptomyces olivaceiscleoticus* is a relevant species, but it was impossible to identify the species of strain UOF1. Thus strain UOF1 has been designated as Streptomyces sp.

Strain UOF1 has been filed with the Fermentation Research Institute, Agency of Industrial Science and Technology, located at 1-1, Higashi 1-chome, Tsukubashi, Ibaraki-ken, Japan on Mar. 30, 1990 on the basis of the Budapest Treaty, the deposition number being FERM BP-2844.

The microorganisms which may be used for the Process of the present invention may be cultured in a conventional manner applicable to fermentation of microorganisms of Actinomycetes. Thus, both organic and synthetic media may be used so far as they contain appropriate amounts of assimilable sources of carbon, nitrogen and inorganic substances.

Preferred examples of carbon sources which may be used for this process include glucose, starch, dextrin, mannose, fructose, sucrose, lactose, xylose, arabinose, mannitol and molasses. If desired, it is possible to use, for example, various hydrocarbons, alcohols and organic acids, depending upon the assimilability of the microorganism used. The carbon sources may be used solely or in combination.

Preferred examples of nitrogen sources which may be used solely or in combination for this process include ammonium chloride, ammonium sulfate, ammonium nitrate, sodium nitrate, urea, peptone, meat extract, yeast extract, dried yeast, corn steep liquor, soyabean powder and cazamino acid.

It is also possible, if desired, to add to the medium various substances such as, for example, sodium chloride, potassium chloride, magnesium sulfate, calcium carbonate, potassium dihydrogen phosphate, dipotassium hydrogen phosphate, ferrous sulfate, calcium chloride, manganese sulfate, zinc sulfate and copper sulfate. If desired, it is also possible to add to the medium suitable substances capable of promoting the growth of the microorganism or the productivity of the desired compounds UCF1 such as for example, vitamin $B_1$ and biotin.

For fermentation, submerged culturing in liquid medium with shaking is preferred. Culturing may be effected, at a temperature of from 16° to 37° C., preferably from 25° to 32° C. and at a pH of from 4 to 10, preferably from 6 to 8, usually for a period of from 1 to 7 days to accumulate the desired compounds UCF1 in the cultured broth and the cells. During culturing, the pH of the medium may be adjusted by using, for example, an aqueous solution of ammonia or ammonium carbonate.

When the amount of the desired product reaches the maximum, the culturing is discontinued. The isolation of the desired compounds from the cultured broth and cells and the following purification may be effected in a conventional manner which may be used for isolation and purification of metabolic products obtained by fermentation of microorganism, for example, as follows:

The cells are separated from the cultured broth by filtration and extracted with chloroform or acetone. The extracted solution is combined with the filtrate. The combined solutions are passed through a column packed with a polystyrene-type adsorbing agent (Diaion HP20, commercial product of Mitsubishi Kasei K.K., Japan) to adsorb the active material. Elution may be effected by the use of ethyl acetate, acetone and the like. The eluate is concentrated and subjected to silica gel chromatography, high performance liquid chromatography and the like to obtain UCF1 in the form of yellow powders.

In the course of isolation and purification, the desired compounds may be detected, for example, by bioassay using Bacillus subtilis No. 10707, thin layer chromatography and absorption of ultraviolet rays and appropriate colour reactions.

(7) Preparation of UCF1-AX and UCF1-BX:

It is possible to obtain UCF1-AX and UCF1-BX in a conventional manner by subjecting the compounds UCF1-A and UCF1-B respectively to oxidation with a suitable oxidizing agent such as, for example, chromium (VI), lead tetraacetate (IV) and mercury oxide in a solvent such as, for example, acetic acid, benzene, dimethylsulfoxide and pyridine. The solvents may be used solely or in combination.

The amount of the oxidizing agent is preferably from 1 to 10 mol on the basis of the amount of the starting compound. The reaction may be effected at a temperature of from 0° to 50° C. for a suitable period of time (usually 1 to 24 hours) which may vary, depending upon, for example, the amount of the oxidizing agent employed and the reaction temperature.

Progress of the reaction may be monitored, for example, by thin layer or column chromatography. The reaction may preferably be continued until the starting compound is not found in the reaction solution.

The isolation of the desired derivatives from the starting compound and the following purification may be effected by conventional methods of organic chemistry, for example, solvent extraction, column chromatography, thin layer chromatography and preparative high performance liquid chromatography.

The following non-limiting examples illustrate the invention.

EXAMPLE 1

Streptomyces sp. UOF1 (FERM BP-2844) was used as a seed strain. The seed strain was cultured in a seed medium (300 ml) put in a 2 l Erlenmeyer flask at a temperature of 30° C. for 48 hours with shaking (200 r.p.m.). The medium contained Bacto-tryptone (5 g/l; commercial product of Difco. U.S.A.), yeast extract (5 g/l), meat extract (3 g/l), soluble starch (10 g/l), glucose (10 g/l) and calcium carbonate (5 g/l) an had an adjusted pH of 7.2 after sterilization.

A main medium (15 l) was put in a 30 l jar fermenter for culturing the resultant seed (10 v/v % on the basis of the main medium) at a temperature of 28° C. with shaking and aeration (200 r.p.m.;15 l/min). The composition of the main medium was as follows:

soluble starch (50 g); corn steep liquor (30 g); potassium phosphate (0.5 g); magnesium sulfate. 7H$_2$O (0.5 g) and calcium carbonate (5 g) [per l].

The pH of the medium was adjusted to 7.0 with NaOH before sterilization and was left during culturing which was effected for 80 hours. After completion of fermentation, n-propanol (15 l) was added to the cultured broth (28 l) with shaking, which was then filtered to separate the cells and precipitates.

The filtrate was concentrated and diluted with water. The material was passed through a column packed with a polystyrene-type adsorbing agent (10 l; Diaion HP20, commercial product of Mitsubishi Kasei K.K., Japan). After removal of impurities by elution with deionized water and 50% methanol successively, elution was further effected successively by using methanol and ethyl acetate. The eluate was concentrated and water was added thereto, followed by extraction with ethyl acetate. The extracted solution was dehydrated using anhydrous sodium sulfate and concentrated. Then the material was transferred to a column packed with silica gel (BW300, commercial product of Fuji Devison Kagaku K.K., Japan) and developed by using a solvent system of chloroform/methanol (100:1 v/v). The eluate was collected and concentrated.

The concentrated material was subjected to high performance liquid chromatography using a reversed phase silica gel column (YMC R-335-20, commercial product of YMC K.K.,Japan) and a solvent system of methanol/50 mM potassium phosphate (8:2 v/v, pH=7). The eluate was divided into small fractions (each 18 ml). Fraction Nos. 20–21 were collected, combined and passed through a column packed with Diaion HP20 to adsorb the active substance onto the adsorbing agent. The column was washed with water and eluted with methanol to yield UCF1-A (63 mg) in the form of yellow powders.

Separately, fraction Nos 28–32 were treated in a similar manner to that described above to obtain UCF1-B (51 mg) in the form of yellow powders.

UCF1-A and UCF1-B gave an Rf value of 0.38 by thin layer chromatography on silica gel (Art. 5715; commercial product of Merck A.G., Germany) in methanol. The retention times of UCF1-A and UCF1-B were respectively 4.68 and 6.57 minutes when subjected to high performance liquid chromatography using a silica gel column (YMC AM312 ODS, commercial product of YMC K.K., Japan) and a solvent system of 50mM potassium diphosphate/potassium monophosphate (7:3 v/v, pH=7) at a flow rate of 1 ml/min.

EXAMPLE 2

UCF1-A (55 mg) obtained by the method of Example 1 was dissolved in acetic acid (2.5 ml). A 60% aqueous solution (2.5 ml in total) containing chromium (VI) (34 mg) was added to the UCF1-A solution five times every hour at room temperature while stirring the mixture for six hours. After adding 2N hydrochloric acid (22 ml), the reaction mixture was extracted five times with ether (125 ml). The organic layer was collected and dried by using anhydrous sodium sulfate, followed by filtration. The residue was concentrated under reduced pressure. The resultant crude product was subjected to column chromatography using a silica gel column and chloroform to obtain purified UCF1-AX (5.4 mg) in the form of a yellow oil.

EXAMPLE 3

UCF1-B (43 mg) obtained by the method of Example 1 was dissolved in acetic acid (4.0 ml). A 60% aqueous solution (2.0 ml in total) containing chromium (VI) (29 mg was added to the UCF1-B solution four times every hour at room temperature while stirring the mixture for six hours. After adding 2N hydrochloric acid (20ml), the reaction mixture was extracted five times with ether (150 ml). The organic layer was collected and dried by using anhydrous sodium sulfate, followed by filtration. The residue was concentrated under reduced pressure. The resultant crude product was chromatographed in a similar to that described in Example 2 to obtain purified UCF1-BX (4.6 mg) in the form of a yellow oil.

We claim:

1. A compound represented by the following formula:

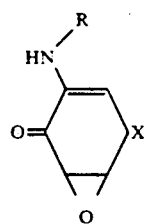
wherein R represents either
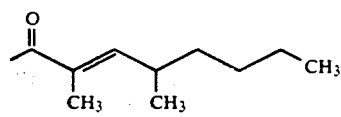
or
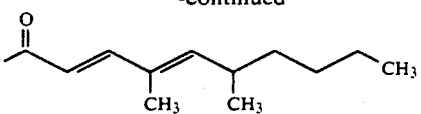
and X represents either
=O    a)
or
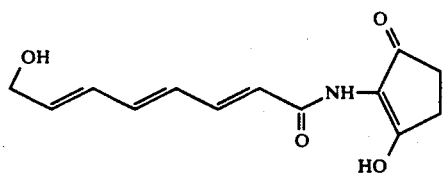
2. A pharmaceutical composition comprising an effective amount of the compound of claim 1 in admixture with a physiological acceptable carrier, dilutant or excipient.
* * * * *